United States Patent [19]

Tibbetts et al.

[11] Patent Number: 5,502,773
[45] Date of Patent: Mar. 26, 1996

[54] METHOD AND APPARATUS FOR AUTOMATED PROCESSING OF DNA SEQUENCE DATA

[75] Inventors: Clark Tibbetts; James B. Golden, III; Deborah L. Torgersen, all of Nashville, Tenn.

[73] Assignee: Vanderbilt University, Nashville, Tenn.

[21] Appl. No.: 88,208

[22] Filed: Jul. 6, 1993

Related U.S. Application Data

[63] Continuation-in-part of Ser. No. 763,457, Sep. 20, 1991, Pat. No. 5,365,455.

[51] Int. Cl.[6] .............................. G06K 9/00; G06F 15/18
[52] U.S. Cl. .......................... 382/129; 382/156; 382/303; 364/413.01
[58] Field of Search .............................. 382/1, 6, 14, 15, 382/41, 49, 129, 156, 303; 395/21, 11; 364/413.01, 413.13; 435/6

[56] References Cited

U.S. PATENT DOCUMENTS

| | | | |
|---|---|---|---|
| 4,484,349 | 11/1984 | McCubbrey | 382/49 |
| 4,841,443 | 6/1989 | Kakumoto et al. | 382/6 |
| 4,972,325 | 11/1990 | Hara | 364/413.01 |
| 4,982,326 | 1/1991 | Kaneko | 364/413.01 |
| 5,121,320 | 6/1992 | Aoki et al. | 382/6 |

OTHER PUBLICATIONS

Murdock et al "Multilayer Perceptron Feature Extractor for Reading Sequenced DNA Autoradiograms" IEEE, Oct. 1991, pp. 562–569.

Guan et al "GRAIL: Integrated Artificial Intelligence System for Gene Recog. and Interp." IEEE Mar. 1992, pp. 9–13.

Wu et al, "Classification Artificial Neural Systems for Genome Research", IEEE Nov. 1992 pp. 797–803.

*Primary Examiner*—Joseph Mancuso
*Assistant Examiner*—Jon Chang
*Attorney, Agent, or Firm*—Waddey & Patterson; Mark J. Patterson

[57] ABSTRACT

A method and apparatus for the processing of DNA sequence image data in real time is implemented using a series of linked neural network processors. As raw image data is received from a sequencing machine, it is buffered and then separately transformed in real time in the processors to enhance the signals indicative of the unknown DNA sequence. A fourth processor receives the transformed data and determines and reports the sequence indicating events.

7 Claims, 11 Drawing Sheets

HIDDEN LAYER ARCHITECTURE

(15 connections)

3 INPUT NODES

3 HIDDEN LAYER NODES

2 OUTPUT NODES

NO HIDDEN LAYER ARCHITECTURE

(12 connections)

METHOD AND APPARATUS FOR AUTOMATED PROCESSING OF DNA SEQUENCE DATA

This invention was made in part from government support under Grant No. HG-00562 from the National Institutes of Health, National Center for Human Genome Research. The government has certain rights in the invention.

This is a continuation-in-part of Applicant's U.S. patent application Ser. No. 07/763,457, filed Sep. 20, 1991, now U.S. Pat. No. 5,365,455.

BACKGROUND OF THE INVENTION

The present invention relates generally to the automated determination of the nucleic acid sequence of a polynucleotide, such as DNA. More particularly, the method and apparatus of the present invention relates to automated, real-time processing of raw scanned image data acquired and generated by scanning automated DNA sequencers and similar devices.

Commercially available automated DNA sequencers generate a large image of DNA sequencing gels, in which the components of individual samples are often labelled with fluorescent or radioactive probes. Densitometric film scanners digitize images of sequencing ladders from films or autoradiograms, which are exposed and developed after fixed periods of electrophoresis. Other systems have fixed or scanning detectors which monitor electrophoretic transport of labeled oligomers through the gel, generating digital images of sequencing ladders in real time. In a typical conventional sequencer of this second type, a digital image file of about twenty megabytes is created, representing analysis of up to forty-eight samples over ten to sixteen hours of electrophoresis. Both classes of sequencing instrument use computer software to translate the raw scanned image dam, i.e., the digitized images of the sequencing ladders, to specific DNA sequences.

The prior art methods implemented in commercially available base-calling software typically initiate a scan of the ladder image to locate the trace of the next oligomer in the sequence, then evaluate the particular attributes of that oligomer's image which identifies its terminal nucleotide. Some real-time systems and film scanners use single labeled oligomers in familiar arrays of four parallel ladders, to spatially discriminate among the four possible terminal nucleotides. Other real-time scanning instruments employ selective band-pass filters for spectroscopic discrimination of four base specific fluorescent labels on the terminal nucleotides. The Applied Biosystems 373A automated DNA sequencer is an example of such a machine.

Unfortunately, prior art sequencers and their corresponding nucleic acid sequence data processing methods do not generate final DNA sequences in real time nor do they provide the information necessary to support pattern recognition-based analysis of the sequence data. Accordingly, both the time and accuracy of DNA sequence determination using these prior art methods are less than ideal and, in the case of accuracy, are deficient as compared to the base-calling skills of human experts.

What is needed, then, is a method and apparatus for processing nucleic acid sequence raw image data which is faster, more accurate, and which allows for processing in real time as the raw image data is acquired. Such a method and apparatus are lacking in the prior art.

SUMMARY OF THE INVENTION

An object of the present invention is to provide an apparatus for automatic processing of nucleic acid sequence data which can be used with a variety of commercially available sequencing machines.

Another object of the present invention is to provide nucleic acid sequence data processing apparatus which can be implemented in software or hardware form, and either separately from or integral with a sequencing machine.

A further object of the present invention is to allow the real time, on-the-fly processing of nucleic acid sequence image data, as such data is being generated by a conventional scanning sequencing machine.

Yet another object of the present invention is to improve the speed and accuracy of nucleic acid sequence determination while using existing sequencing machines.

These and other objects are achieved in a method and apparatus for processing of data for determination of nucleic acid sequences and for genotype mapping. The invention enables real-time processing of multi-channel, pseudo-raster images of DNA sequencing ladders and DNA (or RNA) fragment sizing gels.

The method and apparatus can operate in real-time, with limited memory requirements and high throughput, in such a manner that raw data acquisition continues unimpeded. The apparatus features a cascade processor which has a plurality of operatively linked modules which sequentially and separately perform a signal enhancement transformation operation on each incrementally scanned line of pseudo-raster images generated by an automated gel scanning instrument or scanning film densitometer.

Each module includes both a small memory buffer and a processor. Once filled with data, each module transforms its limited window of signal enhanced data to a new line of data for entry into the memory buffer of the next module. As each full window of data is processed, the memory buffer rolls down to allocate memory for the next incoming line of data. No processing takes place until the memory buffer for that module has been filled. Preferably, the processor in each module is a neural network which has been trained to perform, in serial order, a background subtraction, signal conditioning, and an event filtering transformation operation on the image data received from the preceding module, thereby enhancing the event indicating signals in such data.

BRIEF DESCRIPTION OF THE DRAWINGS

FIG. 9b is a graphical representation of the target vectors for the output of the second module of the present invention, represented as a data stream, for the data shown in FIG. 9a.

DESCRIPTION OF THE PREFERRED EMBODIMENT

General Description of Method and Apparatus

Figure 1:
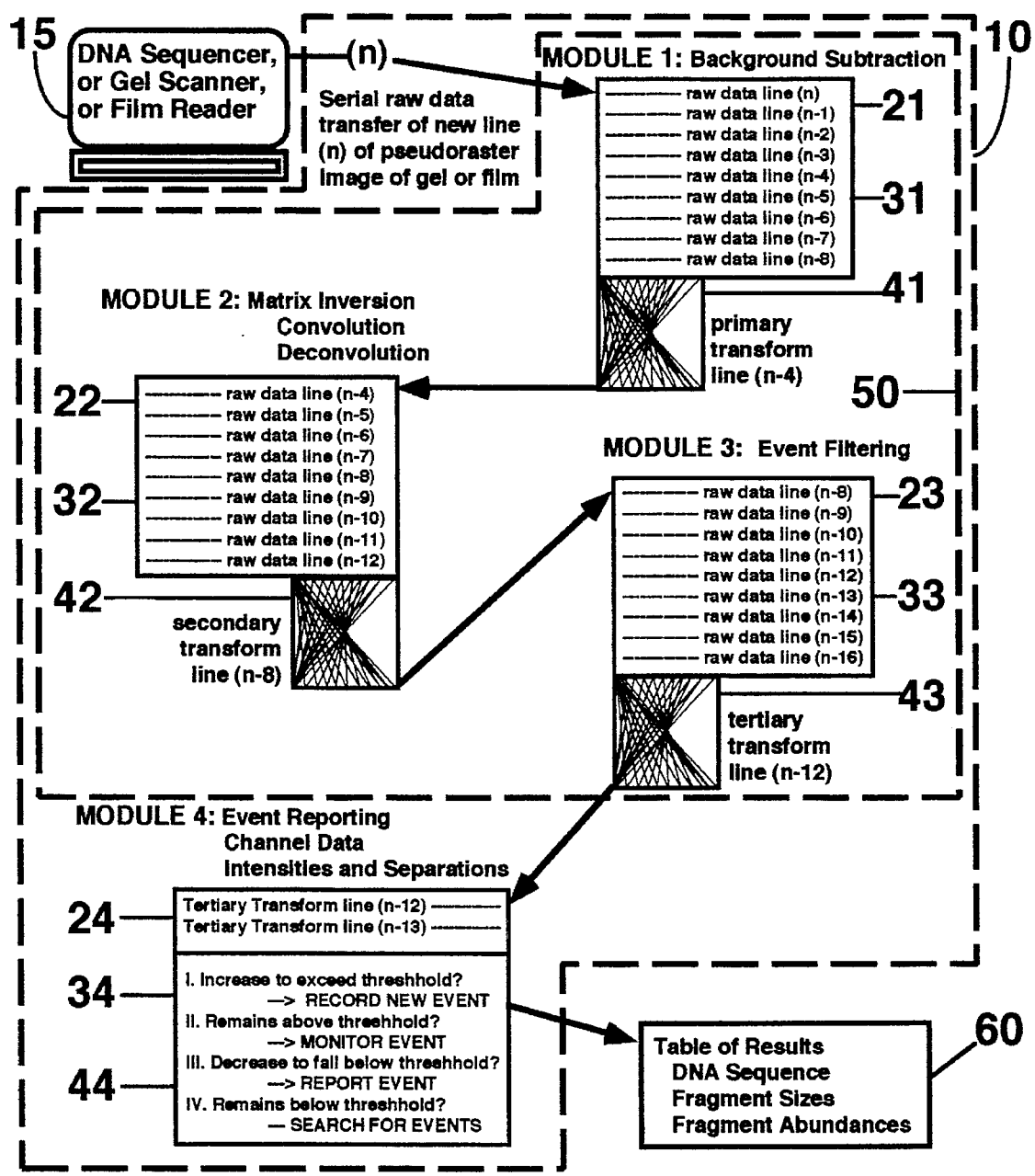
FIG. 1 is a block diagram representation of the apparatus of the present invention, operatively interposed as an interface between a conventional automated DNA sequencer and a sequence display or storage device.

Looking at FIG. 1, the DNA sequence data processing method of the present invention is implemented by a sequence image data processing apparatus 10 which receives raw scanned image data from a separate scanning sequencing instrument 15. Such scanned image data is representative of the nucleic acid sequence of the sample material and, depending on the precise nature of instrument 15, may have undergone some minimal level of processing before transmission to apparatus 10. Alternatively, apparatus 10 can be integral to scanning instrument 15.

Apparatus 10 includes a cascade processor 50 having first, second, and third modules 21, 22, and 23, which are used as means for successively performing signal enhancing transformation operations on the raw scanned image data. A fourth module 24 receives transformed data from cascade processor 50 for purposes of determining the events (e.g., polynucleotide base-calling) indicated by such data. Each module 21, 22, 23, and 24 includes a processor 41, 42, 43, and 44 which is operatively linked to a memory buffer 31, 32, 33, or 34.

At the beginning of DNA sequence data acquisition and processing, or after a clear-buffers command re-initiates the process, scanning instrument 15, such as a DNA sequencer or scanner of gels or films, provides a first full cycle of scanned data, preferably comprising conventional bit mapped data corresponding to one line of a pseudo-raster image. The method then proceeds generally in accordance with the following steps:

1) Raw scanned data line 1 is entered into line 1 of memory buffer 31 of first module 21. No processing takes place.

2) Raw scanned data lines 2 through 9 are sequentially entered into the corresponding lines of buffer 31 of first module 21.

3) Now filled with raw data lines 1 through 9, first processor 41 evaluates the memory state of its corresponding buffer 31, reporting a transformed line structure (first transformation operation), corresponding to raw scanned data line 5, to the first position in memory buffer 32 of second module 22.

4) First memory buffer 31 rolls down, dropping raw data line 1, and raw data line 10 is entered. Buffer 31 now represents lines 2 through 10, and first processor 41 performs a first signal enhancing transformation operation on the raw data and sends a first transformed data line corresponding to raw data line 6 to the second position of second buffer 32 of second module 22.

5) Step 4 is repeated, until the nine lines of second memory buffer 32 are filled with first transformed image data corresponding to raw scanned data lines 5 through 13. Now filled, second processor 42 evaluates the state of second memory buffer 32, performs a second signal enhancing transformation operation on the first transformed image data, and reports a second transformed data line structure corresponding to raw data line 8 to the first position of third memory buffer 33 of third module 23.

6) Steps 4 and 5 are repeated, until the nine lines of third memory buffer 33 are filled with the second transformed image data corresponding to raw scanned data lines 8 through 16. Now filled, third processor 43 evaluates the state of third memory buffer 33, performs a third signal enhancing transformation operation on the second transformed image data, and reports the resulting third transformed data line structure as the finally processed (third transformed) data output of the cascade processor 50.

7) From this point (after the 16 scans for initialization), the series of first, second, and third in-line modules 21, 22, and 23 act collectively as cascade processor 50. With each new line of raw scanned data entered into first module 21, a new line of first transformed data is passed to second module 22, which in turn passes a new line of second transformed data to third module 23, which in turn passes on a new line of third transformed data as fully processed data output. The entire process operates in real time, concurrently with the rate of raw scanned data acquisition, with a short lag corresponding to the narrow window composed of 16 scans.

In the preferred embodiment, the method of the present invention provides the DNA sequence from four parallel raw scanned data streams, representing either of the two typical data presentations of DNA sequencing ladders: (1) oligodeoxynucleotides tagged on their 3' ends with a single radioactive or fluorescent or chemiluminescent label in four parallel base-specific lanes of the gel; or (2) individual oligonucleotides tagged on their 3' ends with four different and visually distinguishable fluorescent or chemiluminescent labels, each label corresponding to only one of the four separate nucleotide bases found in an oligonucleotide, with all four individually labelled oligonucleotides run simultaneously in one lane of the gel.

Accordingly, first module 21 accepts the raw scanned image data stream as serial input from scanning instrument 15, and once its corresponding memory buffer 31 is filled, first processor 41, preferably a neural network processor, performs a first signal enhancing transformation operation, preferably background subtraction, on the four raw data streams. First transformed data output from first module 21 is passed to memory buffer 32 of second module 22, one line at a time, as raw data is received from instrument 15.

Second module 22 accepts the first transformed data stream from first module 21, and once memory buffer 32 is filled, second neural network processor 42 performs a second signal enhancing operation, preferably signal conditioning, on the first transformed (background subtracted) image data. Such signal conditioning operation can include fluorescent color separation (analogous to a photometric matrix inversion), convolution (analogous to peak shape modeling), and deconvolution (analogous to signal resolution enhancement). The second transformed data output from second module 22 is passed to memory buffer 33 of third module 23, one line at a time, as raw data is received from instrument 15 and passed through modules 21 and 22.

Third module 23 accepts the second transformed data stream from second module 22, and once memory buffer 33 is filled, third neural network processor 43 performs a third signal enhancement transformation operation, preferably an extended modeling of the traces of each oligomer as a discrete event (signal traces to model delta functions, analogous to a low pass noise filter).

Third transformed image data output from third module 23 is passed from cascade processor 50 one line at a time to memory buffer 34 of fourth module 24, as raw scanned data is received from instrument 15 and passed through modules 21, 22, and 23.

Fourth module 24 receives and monitors the four streams of third transformed data, each of which corresponds to one of the four 3' terminal dideoxynucleotides ddC, ddA, ddG and ddT, to determine if the signal traces in such data rise above, remain above, fall below, or remain below a serial threshold for event reporting, or base-calling. Memory buffer 34 and processor 44 of fourth module 24 support computations of signal intensities and peak centers of acknowledged oligonucleotide events.

The temporal (or spatial) separations of the oligomers, and the relative intensities of the oligomers, are additional informative event indicating parameters which can be computed as part of the operations of processor 44 of fourth module 24. With access to the buffered raw and transformed data buffers of the preceding modules, these informative parameters can be evaluated without distortion or corruption. Contextual arrays of multiple informative parameters of oligonucleotides in DNA sequencing ladders can be further processed by a pattern recognition method and apparatus to realize enhanced accuracy of the DNA sequence determinations, such as the method disclosed in applicant's co-pending U.S. patent application Ser. No. 07/763,450, filed Sep. 20, 1991, which is incorporated herein by reference.

The preferred embodiment of the present invention uses four data streams representing a single cross-section in time through the pseudo-raster image of a sequencing gel. The memory buffers 31, 32, 33, and 34 of each module 21, 22, 23, and 24 can be linearly expanded to represent each of multiple lateral positions in the window of scanning instrument 15. Each processor 41, 42, 43, and 44 would then serially process the blocks of data corresponding to successive scanner positions, and pass the transformed data to corresponding addresses of the memory buffer of the succeeding module.

Data throughput in the embodiment described herein can be supported by conventional microprocessors, implemented in either software or hardware, without creating a data processing bottleneck that would interfere with the continuous process of raw image data acquisition.

Architecture of the Cascade Processor

Each module 21, 22, and 23 of cascade processor 50 serially processes the current state of its corresponding memory buffer 31, 32, or 33 to a transformed data output line to be passed to the next succeeding module or to be presented as final output, to fourth module 44 for example. The cycle of each process in each module 21, 22, 23 of cascade processor 50 is to:

1) roll down the buffer to allocate memory for the next incoming line of data;

2) feed the refreshed buffer's data through the neural network processor of that module;

3) pass the transformed data output array of the processor to the next succeeding module.

Once the buffers 31, 32, and 33 of cascade processor 50 are filled, each new line of raw image data received from the DNA sequencer or scanner instrument 15 initiates a cascade of processing through the system to produce a corresponding line of output. Each line of output is offset in time by a narrow window of recent scan lines.

Figure 8A:
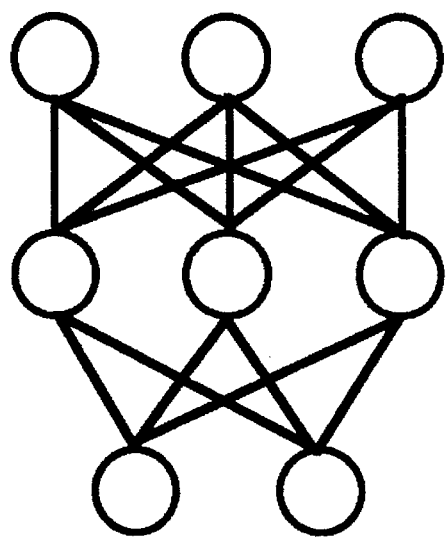
FIGS. 8a and 8b are schematic representations of neural network processors as would be used in the first, second, and third modules of the present invention, using hidden layer architecture or no hidden layer architecture, respectively.

Each neural network processor 41, 42, 43, of each module 21, 22, 23 has a conventional feed forward—backpropagation architecture and is trained in a supervised learning mode, in a manner well known to those skilled in the art of designing and training neural network processors. The architecture of processors 41, 42, 43 may be conventional, with a suitable number of hidden layer nodes between the nodes of the input and output layers, as shown on FIG. 8a.

Figure 7:
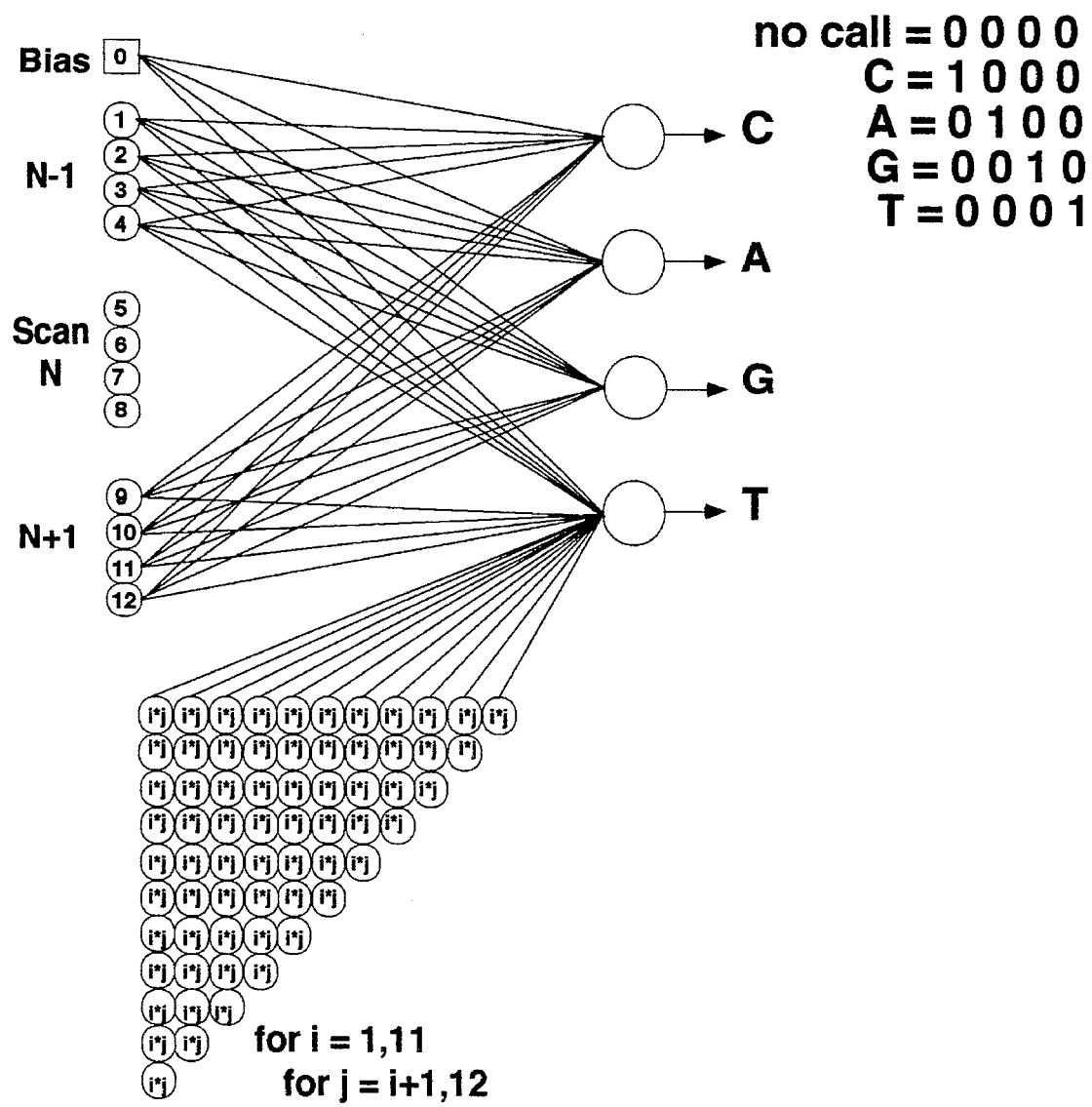
FIG. 7 is a schematic representation of a neural network processor, such as would be implemented in the first, second, and third modules of the present invention, using an array of higher order terms rather than hidden layer nodes.
Figure 8B:
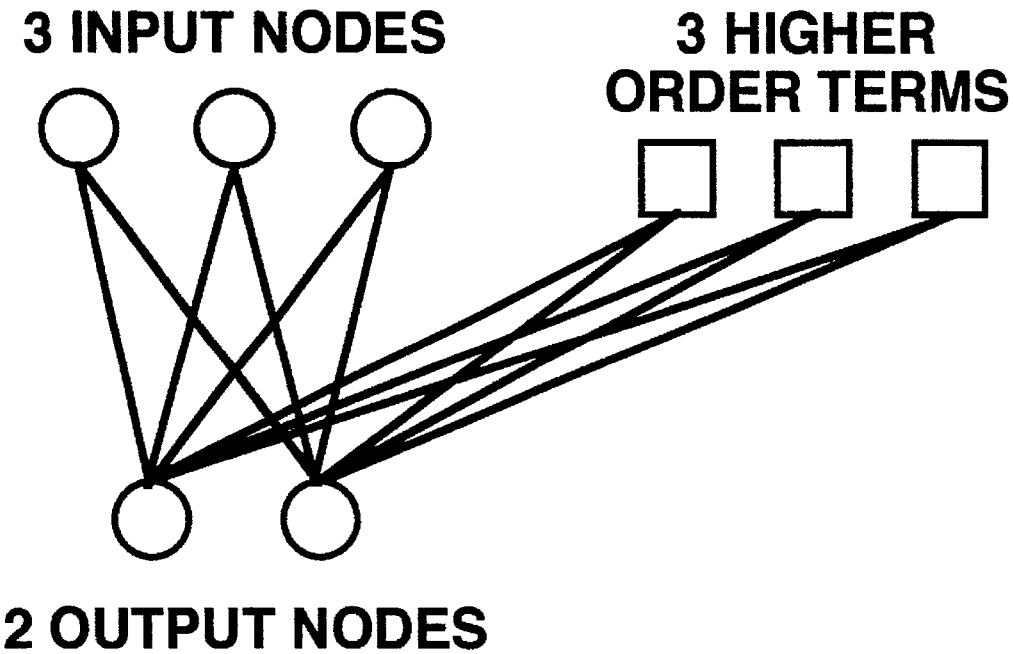

Alternatively, the equivalent number of hidden layer nodes may be represented by an array of higher order terms, such as pairwise products of the different input nodes, as shown on FIGS. 7 and 8b. In the latter case, the higher order dimension of the input vector space enables the processor to operate with no hidden layer nodes, and correspondingly fewer connections to be trained.

In the preferred embodiment, processors 41, 42, 43 have N nodes representing the arguments of the input vector to M nodes representing the arguments of the target output vector. The number of nodes used for the hidden layer or for the higher order term array is $N*(N-1)/2$. This corresponds to the number of pairwise cross-products of the input nodes. The hidden layer architecture has more total connections than equivalent networks with the higher order term array.

A single weight matrix represents the higher order term architecture, with $(N+N(N-1)/2)*M$ connections. Two connection weight matrices represent the hidden layer architecture, with $(N+M)*N(N-1)/2$ connections. As the dimension of the input vector, N, increases, the difference in the number of connections of the two architectures increases as approximately $N^{1.5}$. The dimensions of the weight matrix for the higher order term network are as indicated in the product above. The dimensions of the first and second weight matrices for the hidden layer architecture are, respectively, $N*N(N-1)/2$ and $M*N(N-1)/2$.

The forward processing of input vectors through the networks is easily encoded, as illustrated in the following pseudo-code segment:

Let N= number of input layer nodes, and n is the index of node number.

Let M=number of output layer nodes, and m is the index of node number.

Let K=number of hidden layer or higher order term nodes=$N*(N-1)/2$, and k is the index of node number.

Let output[x]=data value presented for forward processing by node x.

Let weight[x,y]=connection weight values for node x to node y.

Hidden Layer Network:

The hidden layer outputs are evaluated in a first loop (programmed in C or other conventional scientific programming language) as:

```
for (k = 1; k < = K; + + k) {
    sum_inputs = 0;
    for (i = 1; i < = I; + + i) sum_inputs + =
    output[i] *weight[i,k];
    output[k] = 1/(1 + exp(-sum_inputs));
}
```

The output layer outputs are evaluated as a second loop, as:

```
for (m = 1; m < = M; + + m) {
```

```
       sum_inputs = 0;
       for (k = 1; k < = K; + + i) sum_inputs + =
       output[k] *weight[k,m];
       output[m] = 1/(1 + exp(-sum_inputs));
}
```

Higher Order Terms Network:

A first loop evaluates the outputs of the higher order term array as cross-products of the outputs from the primary input nodes, as:

```
/*  x and y are used as dummy indices referring to
    elements of the input node array */
/*  the loop generates output values for K higher order
    term nodes, where K = I*(I − 1)/2 */
    k = 1;
    for (x = 1; x < I; + + x) {
        for (y = x + 1; y < = I; + + y) {
            output[k] = output[x]*output[y];
            + + k;
        }
    }
}
```

A single weight matrix connects the input and higher order term nodes to the nodes of the output array. The outputs of the output array nodes are evaluated as:

```
for (m = 1; m < = M; + + m) {
    sum_inputs = 0;
    for (i = 1; i < = I; + + i) sum_inputs + =
    output[i] * weight[i,m];
    for (k = 1; k < = K; + + i) sum_inputs + =
    output[k] * weight[k,m];
    output[m] = 1/(1 + exp(-sum_inputs));
}
```

First Module Transformation Operation (Background Subtraction)

Raw data from a commercially available sequencing instrument 15 is ordinarily used by software supplied with or integral to instrument 15 to construct a bit map, corresponding to a pseudo-raster image of the sequencing or sizing gel electrophoresis run. In the present invention, this raw scanned image data is transmitted from instrument 15 to apparatus 10. Each raster line of raw data is presented as the input vector to neural network processor 41 of first module 21, to be transformed into corresponding data streams from which background levels have been algorithmically subtracted. The target vectors of first module 21 are determined by subtracting from each data channel the minimum value within a broad range of data surrounding each data value in the channel. It has been determined that a range of 200 scans surrounding each point is suitable for estimation of the data channel background levels and generation of an input-target vector training set. Input vectors preferably will represent windows of the 9 most recent scans.

As an example of how the method and apparatus of the present invention can be adapted for use with an existing DNA sequencing instrument 15, the raw data generated by the ABI Model 373 DNA sequencer, manufactured by Applied Biosystems, Inc. of Foster City, Calif., constitutes data streams of short integers, corresponding to a pseudo-raster bit map of the sequencing gel. A laser-scanner-photometer traverses the scanning window to the gel, monitoring fluorescence in discrete time intervals at each of 194 fixed, lateral positions. A typical run of 12 hours, with the instrument's 6 second scan cycle time, has 7200 recorded scans. Each scan cycle records 4 short integers as photometry values at each lateral position, for a total of 1552 bytes per raster line. These data are stored in a gel image file which has a format of 407 byte fixed length records. The 194 sampling values, for each traverse using one of the four filters, are saved in 388 of the 407 bytes of four successive records. The remaining bytes of each 407 record are informative fields which indicate the filter number (0 to 3), scanner traverse number, and other runtime parameters. The entire bitmap of the pseudo-raster image is typically stored for later processing in a file of about 11.7 megabytes. The entire file is even larger, containing additional information for tracking of the individual samples loaded onto the gel, and perhaps a compressed representation of the gel image.

Serial data transfer from instrument 15 can be intercepted to access the raw photometry values used to construct the bitmap of the pseudo-raster image. Similarly, this data can be recovered from the bitmap itself, or from the individual sample data files which are generated as tracked cross-sections or profiles through the bitmap of the gel image. In individual sample data files, the raw data profiles are accessed through tags or fixed length data records found at the end of the files. Those 28 byte-long records, which are initiated as 'DATA0001', 'DATA0002', 'DATA0003', and 'DATA0004', have long integers encoded in byte 21 through byte 24 of each record. These integers indicate the offset number of bytes from the start of the data file at which the short integer arrays of photometer data are stored. These records represent tandem arrays of the full time series of raw data sampling through filters 0, 1, 2, and 3 of instrument 15, respectively.

Figure 2:
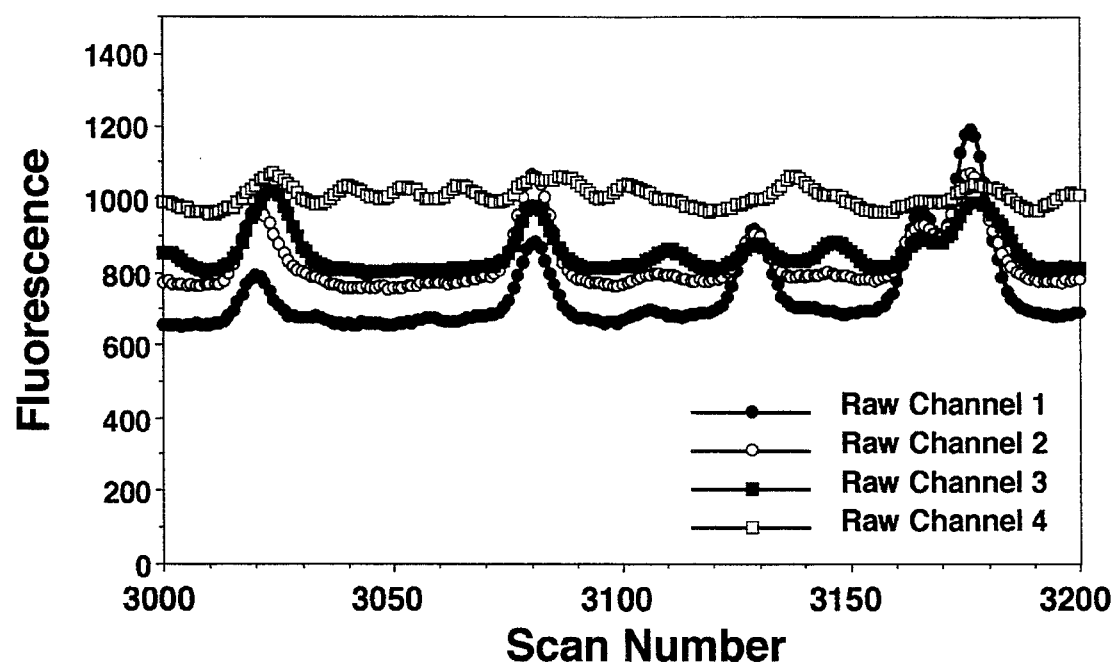
FIG. 2 is a graphical representation of a window of two hundred scans, ranging from scan 3000 to scan 3200, of raw scanned data from an ABI 373A DNA sequencer image data file.
Figure 3:
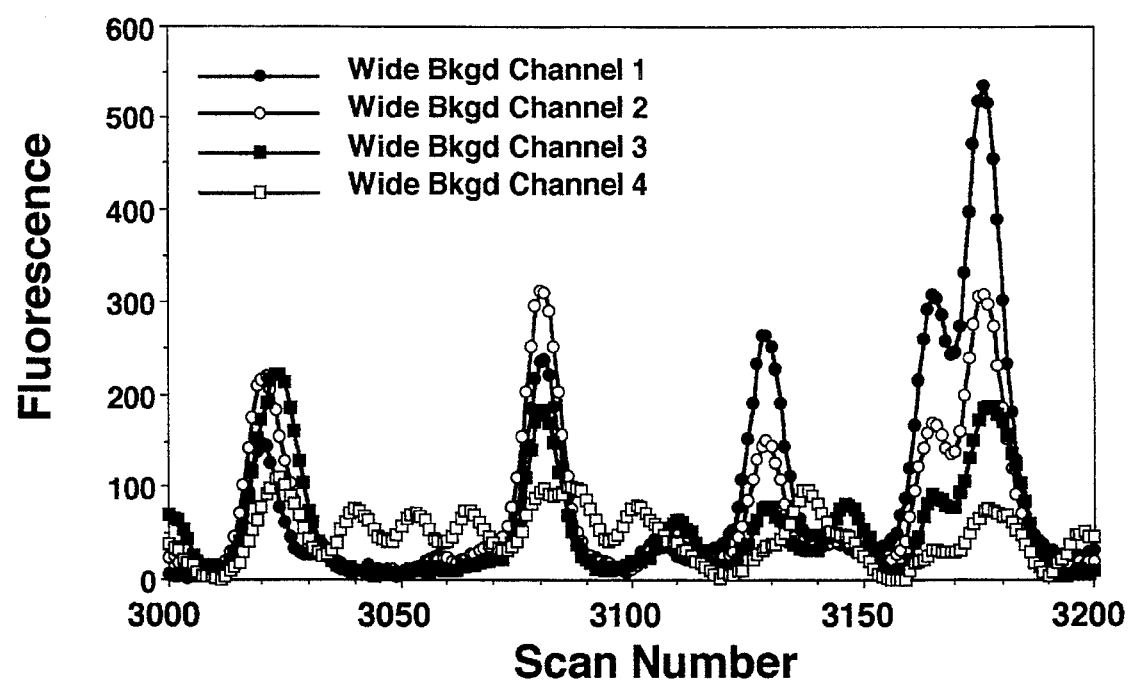
FIG. 3 is a graphical representation of the raw image data of FIG. 2, after algorithmic background subtraction as achieved in a prior art data processing apparatus and method.

FIG. 2 illustrates a window of 200 scans of raw data from an ABI 373A data file. In this unprocessed state, the background signal levels are large relative to signal variations, but the background variation itself is small. FIG. 3 illustrates the same data after a conventional algorithmic background subtraction is applied to the four data streams. The value of each raw data point in the four raw data streams is reduced by the minimum value within a broad window (200 scans) surrounding the position of that point in its respective data stream.

Using data from sets of 9 successive scans of the four data channels, a higher order term embodiment of first neural network processor 21 is trained. The 36 primary input nodes are expanded to a cross product array of 36*35/2=630 higher order terms. These expanded input vectors were then mapped through 2520 connections to four nodes of the output layer. The target vectors used for training first processor 41 correspond to the fifth scan of each set of 9 input scans using data values generated by the algorithmic background subtraction described in FIG. 3 and above.

Figure 4:
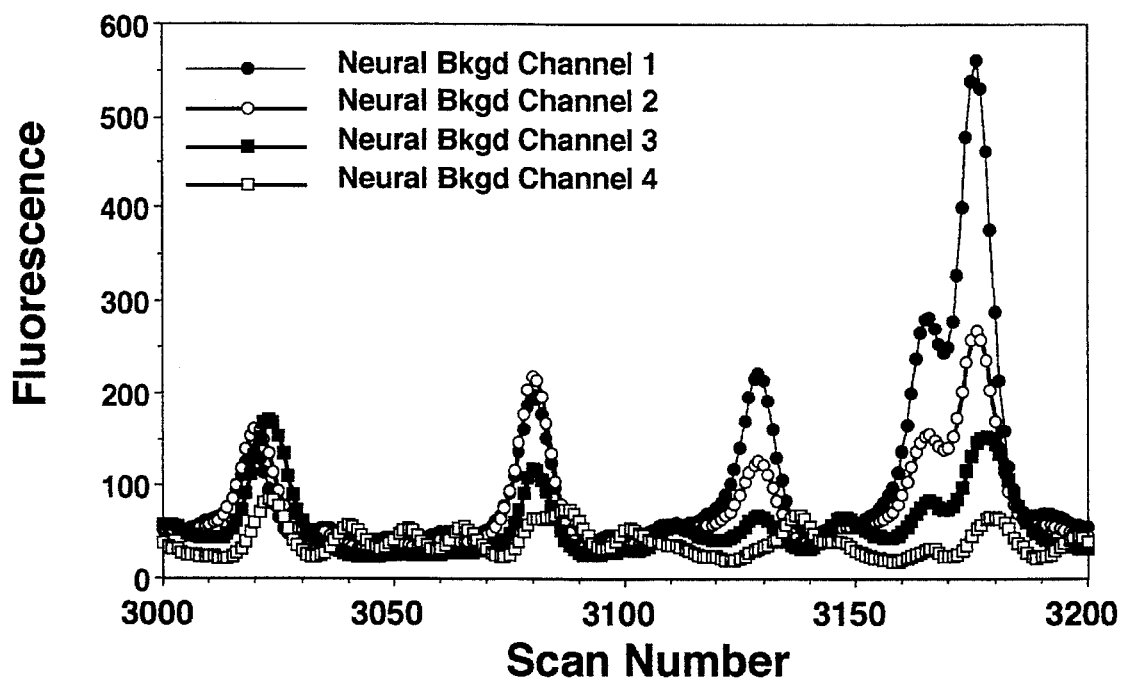
FIG. 4 is a graphical representation of the raw scanned image data of FIG. 2, after a background subtraction transformation operation has occurred in the first module of the apparatus of the present invention.

Once trained, processor 41 is operated in feed-forward or cascade mode, through all successive 9-scan windows of raw data from a DNA sequencing ladder not used for training. FIG. 4 shows the first transformed data output from first processor 41 for scans 3200 to 3300 of this DNA sequencing ladder. The identities of 17 deoxynucleotides (dA, dC, dG or dT) appearing in this interval are indicated above their respective signal traces. The similarity of the data stream profiles shown in FIG. 3 and FIG. 4 confirms the utility of carrying out neural network background substraction as a first image data transformation operation in first module 21 of cascade processor 50.

Second Module Transformation Operation (Signal Conditioning, including Color Separation, Convolution, Deconvolution)

Figure 9A:
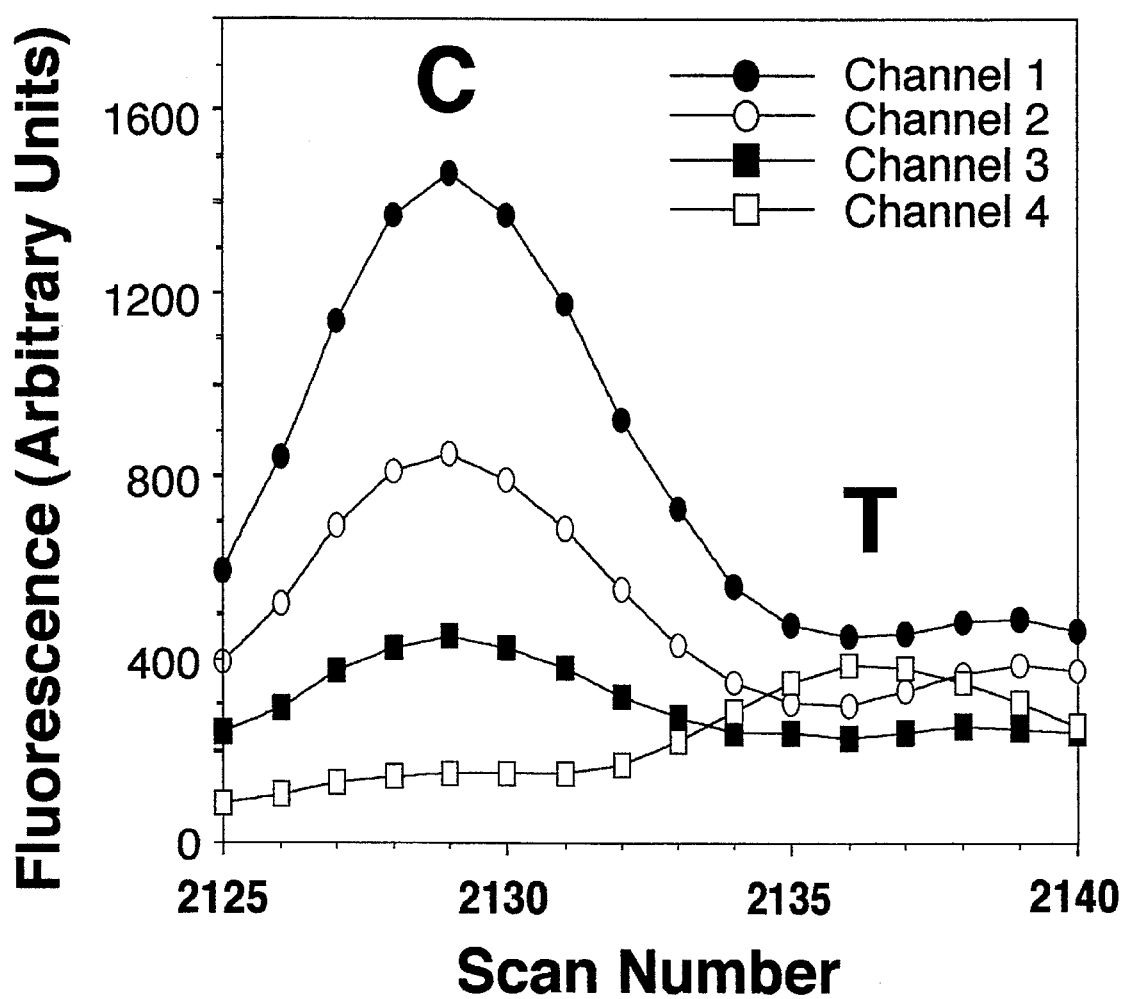
FIG. 9a is a graphical representation of signal traces of two oligomers, -dC, -dT, as would be used in the training of the second module of the present invention, after background subtraction.
Figure 9B:
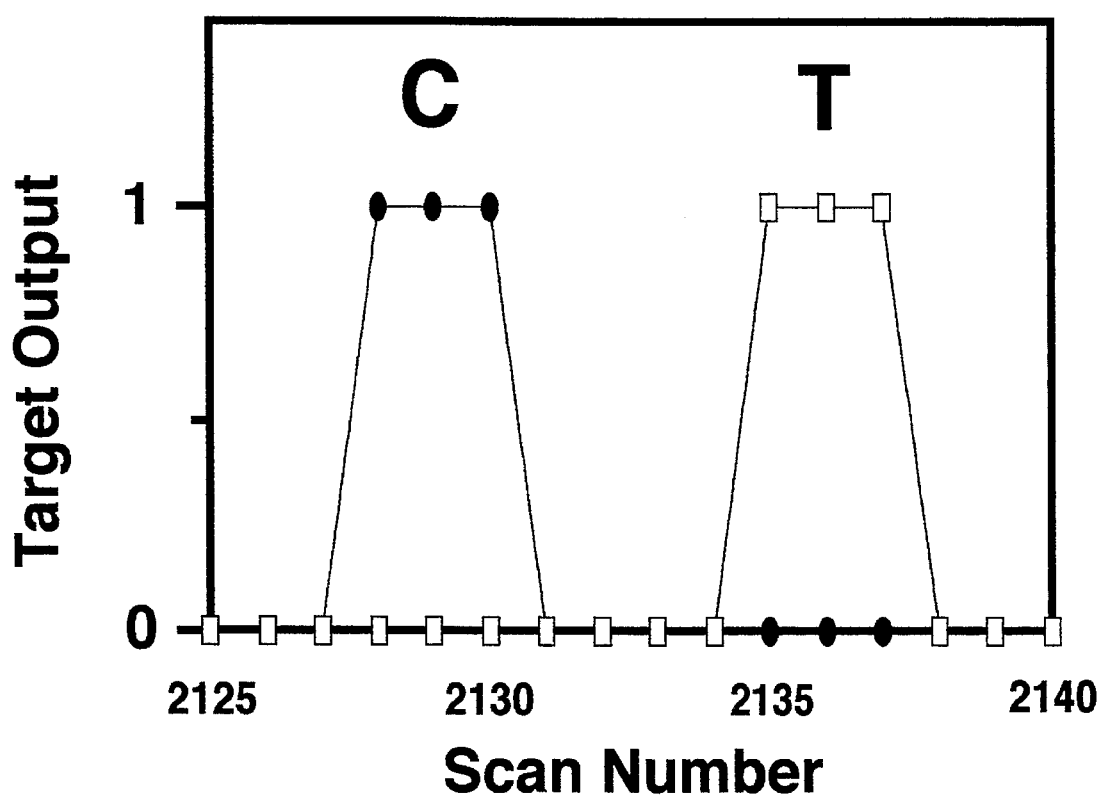

The training of neural network processor 42 of second module 22 requires specification of the particular DNA sequences represented in the training data sets. To accomplish this, DNA sequencing ladders representing HaeIII restriction fragments of the phage ΦX174 genome, cloned into the phage vector M13mp18, and sequences derived from the cloning-sequencing vector itself, can be used. The traces of oligomers in the four data streams correspond to the known DNA sequence, and these are readily identified by inspection. Simple step functions (or discrete Kronecker $\partial$ can be employed for target vectors, as illustrated in FIG. 9a, which shows the traces of two oligomers, -dC-dT-, in the background-subtracted data streams. The target vectors (as data streams) are shown in FIG. 9b, as three points having a value of 1, superimposed on the scan positions of the peak signals of the oligomer traces. All other values of the target vectors are 0, except in the channel corresponding to the particular nucleotide identity.

Figure 5:
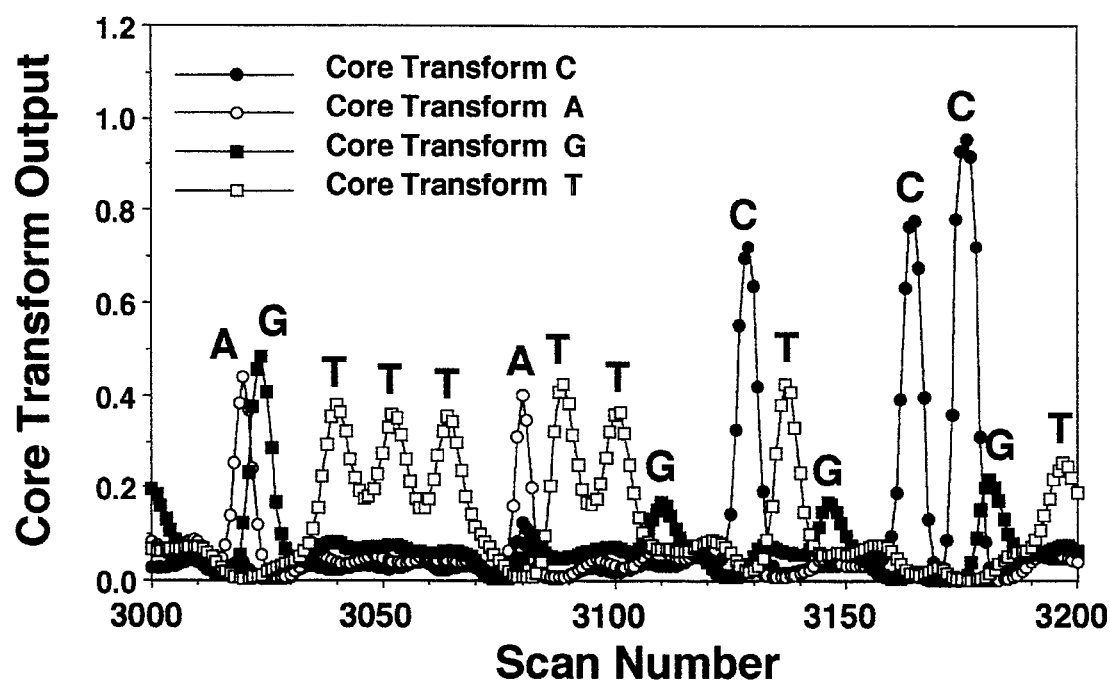
FIG. 5 is a graphical representation of the raw scanned image data of FIG. 2, and first transformed data of FIG. 4, after execution of a signal conditioning transformation operation in the second module of the apparatus of the present invention.

In this embodiment, neural network processor 42 of second module 22 is trained with data representing several DNA sequencing ladders, with 28 input nodes representing a window of seven successive scans of background subtracted data. Each input vector is expanded to a higher order term array of 28*27/2=378 nodes. The input vectors are mapped to four output nodes representing the four nucleotides: dC, dA, dG, and dT. Values of the target vectors are given by the 3-scan wide step functions appearing as value 1 in the appropriate output channel, centered on the 7 scan wide input window. FIG. 5 illustrates the results of a second image data transformation operation, here signal conditioning, in trained second module 22, performed on the first transformed (background subtracted) data displayed in FIG. 4.

Second module 22 transforms the background subtracted data streams into a series of discrete event signals, singularly representing the specific nucleotides of the sequence. These second transformed data streams can be used to specify the DNA sequences by well known peak-finding procedures. The DNA sequence is given as the time order of qualified events revealed by screening the processor outputs of each of the four second transformed data streams.

The outputs of processor 42, after signal conditioning, can be used to generate an inner product with the raw data, as an estimate of the relative intensity of the oligomer event. This inner product is the simple sum of products of an output channel and its corresponding raw data input channel, scan by scan over the interval of significant signal from the output channel. This estimate of oligomer intensity can also be used to calculate a weighted average of the scan numbers during the period of data collection for an oligomer event. For n scans, representing an oligomer event:

$r_i$ = Raw data input for scan $i$
$t_i$ = transformed output for scan $i$ $$\text{Oligomer Intensity} = \sum_{i=1}^{n} (r_i * t_i)$$

$$\text{Oligomer Time of Flight from Well to Detector} = \sum_{i=1}^{n} (i * r_i * t_i) / \sum_{i=1}^{n} (r_i * t_i)$$

FIG. 7 illustrates a single layered neural network having higher order input terms used for a second image data transformation operation, in this case signal conditioning, as implemented in processor 42. The input nodes 1–12 represent the four channels of photometry data from three successive scans of an automated DNA sequencer across the sample lane. Pairwise products of the input terms comprise the sixty-six nodes of the higher order input array. All of the seventy-nine input node (not all connections are shown) are fully connected to the four nodes of the output layer.

In the preferred embodiment of the present invention, the process of feature extraction and event reporting (e.g., base-calling) is postponed for execution in fourth module 24, following an event filtering operation in third module 23 which enhances the identification of the oligomers.

Third Module Transformation Operation (Event Filtering)

The discrete signal traces in the second transformed data streams from second module 22 are further transformed and enhanced in third module 23. In the preferred embodiment, the input data vector for third module 23 comprises a window of 11 scans from one of the four output streams from second module 22. These 11 input nodes are expanded to a higher order term array of 11*10/2=55 nodes. The input vectors are mapped to a single output node target using the same step function or delta function targets from the corresponding nucleotide specific data stream. The third transformation process of third module 23 operates as an event filter (low pass noise filter), transforming the discrete signals in the output streams from second module 22 to signals more closely approximating the desired step function target.

Figure 6:
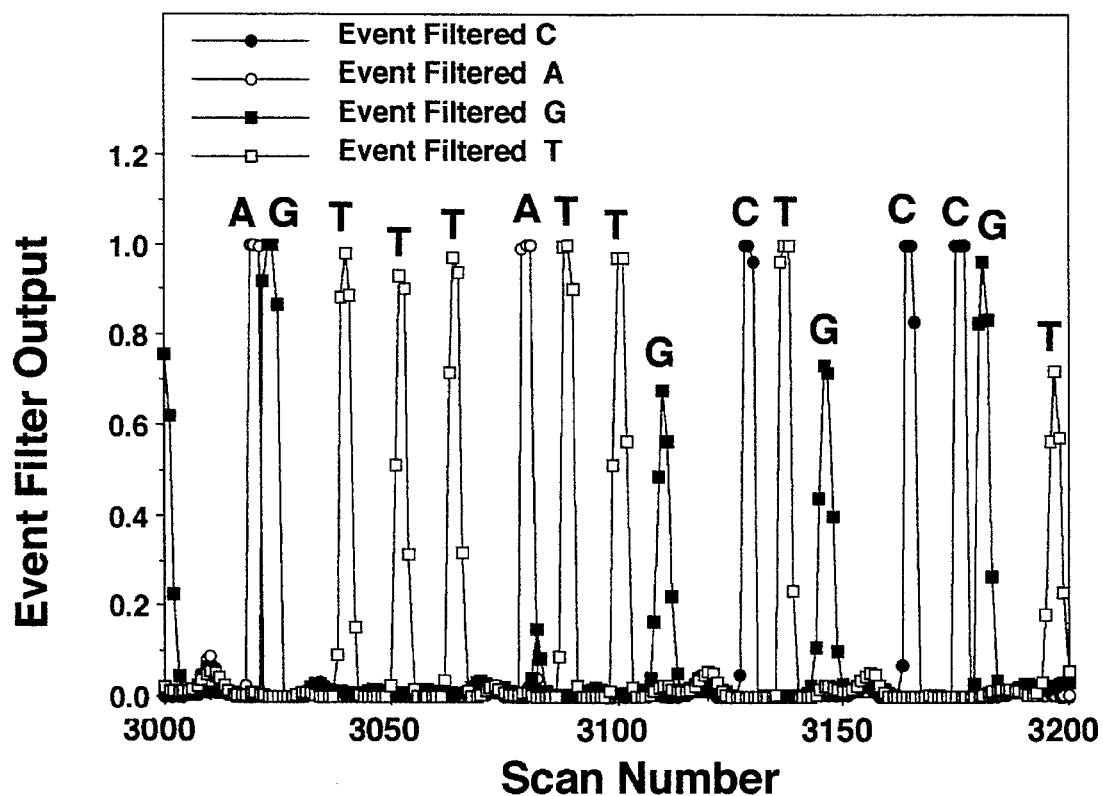
FIG. 6 is a graphical representation of the output of the cascade processor of the present invention, after the event indicating signals in the data of FIGS. 2, 4, and 5 have been further enhanced by an event filtering transformation process in the third module of the present invention.

FIG. 6 illustrates the third transformed data output from a trained neural network processor 43 in third module 23, using the same window of data from the sequencing ladder as shown in FIGS. 2, 4 and 5. It will be apparent to those skilled in the art that unambiguous base-calls can be made in the proper sequence by discrimination of the now well resolved event signal traces in the third transformed data output streams.

Fourth Module Processes (Event Reporting)

Processor 44 of fourth module 24 is not a neural network, but rather a conventional processor performing peak-finding and feature extraction on one or more of the transformed data streams generated in the preceding cascade processor 50. The temporal order of the detected oligomers provides a first pass estimation of the DNA sequence. The yield and the separation of an oligomer in a sequencing gel provide information about the 3' nucleotide identity, based upon independent biochemical and biophysical determinants.

An estimate of the relative yield of the oligomer event can be made from the intensity of its signal in the data streams. This intensity is determined from the outputs of cascade processor 50 as an inner product with the raw data. The separation of successive oligomers in the ladder is estimated as the difference in time (scan numbers, six seconds for first scan) between their peak centers.

Cascade processor 50 could accurately track the time-of-flight, from well to detector, for each of the oligomer events in the cumulative feature table generated during a sequencing run. The output of cascade processor 50 does not alter the temporal separations of oligomers reflected in the raw data streams, as do many prior art automated DNA sequencing data processors and methods.

The steps of the method carried out in cascade processor 50 and apparatus 10 of the present invention are most readily implemented as software, as within a microcomputer or workstation handling the incoming serial data stream from the DNA sequencer, gel scanner or film reader.

Alternatively, the serial raw scanned image data may be processed on-the-fly in real time, by a dedicated hardware interface apparatus 10. Such an apparatus can be constructed as a hardwired series of modules 21, 22, and 23 containing neural network processors 41, 42, and 43, with weights determined from the training and analysis described above. Another embodiment of apparatus 10 would include an interface board having an EPROM and microprocessor for expression of the neural network processors 41, 42, and 43, and to handle the input and output functions. The EPROM would have the advantage of updating of weight matrices used in cascade processor 50. The application of thin gels or capillary gel arrays promises to accelerate the electrophoretic separations of DNA sequencing ladders, and the hardware format of cascade processor 50 may be essential to keep pace with the scanning instrument 15.

Further improvement of gel-scanning digital image acquisition systems is leading to larger and larger raw image files. A CCD camera system can be used to follow fluorescence-labels in a sequencing or sizing gel format. Typical CCD chips can support a 512×512 pixel array with 16 bit depth, recording a 0.5 Mbyte download every second. A high voltage, thin gel sequencing run of 2 hours would produce a pseudo-raster image file of about 3.8 gigabytes. This image would be the record of perhaps 100 or more DNA samples, yet it would be impractical to store the raw data image. On-the-fly processing and reporting of the samples' DNA sequences would be preferred, a method supported by the present invention.

It will also be apparent to those skilled in the art that the method and apparatus of the present invention can also be used in conjunction with DNA fragment sizing experiments, for purposes of clinical diagnostics, forensic application of DNA sequence determination methods, and gene mapping.

Thus, although there have been described particular embodiments of the present invention of a new and useful method and apparatus for automated processing of DNA sequence data, it is not intended that such references be construed as limitations upon the scope of this invention except as set forth in the following claims. Further, although there have been described certain operational parameters used in the preferred embodiment, it is not intended that such be construed as limitations upon the scope of this invention except as set forth in the following claims.

What is claimed is:

1. An apparatus for processing of raw image data from a polynucleotide sequencing machine comprising:
    a. first, second, and third modules sequentially and operatively linked together to define a cascade processor means for performing a series of transformation operations on said raw image data, each of said transformation operations including steps for enhancement of nucleic acid sequence signals contained in said raw image data; and
    b. each of said first, second, and third modules comprising a memory buffer and a neural network processor, wherein each of said modules implements one of said transformation operations.

2. The apparatus of claim 1 wherein said transformation operation performed in said first module comprises background subtraction, said transformation operation performed in said second module comprises signal conditioning, and said transformation operation performed in said third module comprises event filtering.

3. The apparatus of claim 1 further comprising a fourth module for receiving transformed data from said cascade processor means, said fourth module comprising means for processing enhanced nucleic acid sequence signals contained in said transformed data.

4. The apparatus of claim 3 further comprising an interface board containing said cascade processor and said fourth module, and means contained on said interface board for receiving said raw image data directly from said polynucleotide sequencing machine.

5. The apparatus of claim 4 further comprising means contained on said interface board for receiving and processing said raw image data in real time as it is generated by said polynucleotide sequencing machine.

6. A method of automatically processing raw nucleic acid sequencing image data scanned in a polynucleotide sequencing machine, said raw image data including signals representative of a nucleic acid sequence, comprising the steps of:
    a. transmitting said raw image data to the input of a first processing module;
    b. performing a first signal enhancement transformation operation in said first module, thereby generating first transformed image data at the output of said first module;
    c. transmitting said first transformed image data to the input of a second processing module;
    d. performing a second signal enhancement transformation operation on said first transformed image data in said second module, thereby generating second transformed image data at the output of said second module;
    e. transmitting said second transformed image data to the input of a third processing module;
    f. performing a third signal enhancement transformation operation on said second transformed image data in said third module, thereby generating third transformed image data at the output of said third module.
    g. wherein said first, second, and third modules receive multiple lines of image data corresponding to multiple scans of said sequencing machine, and temporarily store said multiple lines of image data in a buffer before performing said first, second, and third transformation operations; and
    h. wherein said first transformation operation comprises background subtraction, said second data transformation operation comprises signal conditioning, and said third transformation operation comprising event filtering.

7. The method of claim 6 further comprising the step of processing said third transformed image data to extract and report a series of events indicative of a nucleic acid sequence corresponding to said signals in said raw scanned image data.

* * * * *

UNITED STATES PATENT AND TRADEMARK OFFICE
CERTIFICATE OF CORRECTION

PATENT NO. : 5,502,773
DATED : March 26, 1996
INVENTOR(S) : Clark Tibbetts, et. al.

It is certified that error appears in the above-identified patent and that said Letters Patent is hereby corrected as shown below:

Title page, item [75] Inventors: insert-- Jacob C. Martin, Jr.--

Signed and Sealed this

Thirteenth Day of August, 1996

Attest:

BRUCE LEHMAN

Attesting Officer

Commissioner of Patents and Trademarks